(12) United States Patent
Komata et al.

(10) Patent No.: US 7,598,413 B2
(45) Date of Patent: Oct. 6, 2009

(54) PROCESS FOR PRODUCING FLUORINE-CONTAINING ALKYLSULFONYLAMINOETHYL α-SUBSTITUTED ACRYLATE

(75) Inventors: Takeo Komata, Kawagoe (JP); Ryo Nadano, Saitama (JP); Makoto Matsuura, Iruma-gun (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 12/187,823

(22) Filed: Aug. 7, 2008

(65) Prior Publication Data

US 2009/0069595 A1    Mar. 12, 2009

(30) Foreign Application Priority Data

Sep. 11, 2007    (JP) .............................. 2007-235143

(51) Int. Cl.
C07C 69/52    (2006.01)

(52) U.S. Cl. ...................................................... 560/222

(58) Field of Classification Search ................. None
See application file for complete search history.

(56) References Cited

U.S. PATENT DOCUMENTS

| | | | |
|---|---|---|---|
| 6,165,678 A | 12/2000 | Allen et al. | |
| 6,949,325 B2 | 9/2005 | Li et al. | |
| 7,115,771 B2 * | 10/2006 | Komata et al. | 560/222 |

FOREIGN PATENT DOCUMENTS

| | | | |
|---|---|---|---|
| JP | 2005-281301 A | | 10/2005 |
| JP | 20005281301 A | * | 10/2005 |

OTHER PUBLICATIONS

Barthel-Rosa et al, Coordination Chemistry Reviews, Chemistry in Fluorous Media: A User's Guide to Practical Considerations in the Application of Fluorous Catalysts and Reagents, 1999, 190-192, pp. 587-605.*
"Fluorine Chemistry", Kodansha Scientific Ltd., 1979, pp. 75-76.

* cited by examiner

Primary Examiner—Paul A Zucker
(74) Attorney, Agent, or Firm—Crowell & Moring LLP

(57) ABSTRACT

There is provided a process for producing a fluorine-containing alkylsulfonylaminoethyl α-substituted acrylate of the formula [3] by reaction of an aminoethyl α-substituted acrylate of the formula [1a] with a fluorine-containing alkylsulfonic fluoride of the formula [2], or by reaction of an aminoethyl a-substituted acrylate salt of the formula [1b] with a fluorine-containing alkylsulfonic fluoride of the formula [2] in the presence of a base, wherein a fluorine-containing compound is used as a reaction solvent:

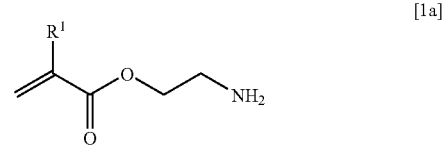

[1a]

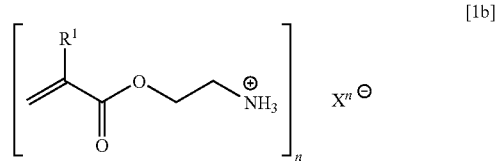

[1b]

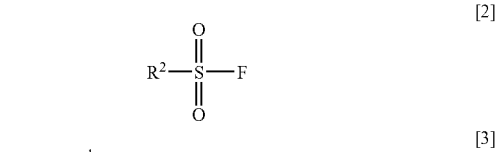

[2]

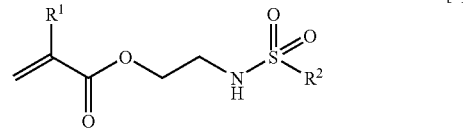

[3]

where $R^1$ is a hydrogen atom, methyl group, ethyl group, n-propyl group, isopropyl group, n-butyl group, sec-butyl group, tertbutyl group, fluoromethyl group, difluoromethyl group, trifluoromethyl group or perfluoroethyl group; $R^2$ is a fluorine-containing alkyl group having a carbon number of 1 to 6; $X^{n-}$ is a counter anion (n is a positive integer); and Y is a fluorine atom, chlorine atom or bromine atom.

9 Claims, No Drawings

PROCESS FOR PRODUCING FLUORINE-CONTAINING ALKYLSULFONYLAMINOETHYL α-SUBSTITUTED ACRYLATE

BACKGROUND OF THE INVENTION

The present invention relates to a process for producing a fluorine-containing alkylsulfonylaminoethyl α-substituted acrylate represented by the general formula [3], which is useful as a monomer for a next-generation photoresist:

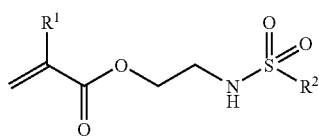

[3]

where $R^1$ is a hydrogen atom, methyl group, ethyl group, n-propyl group, isopropyl group, n-butyl group, sec-butyl group, tertbutyl group, fluoromethyl group, difluoromethyl group, trifluoromethyl group or perfluoroethyl group; and $R^2$ is a fluorine-containing alkyl group having a carbon number of 1 to 6.

Sulfonylaminoethyl α-substituted acrylates are expected to be useful as monomers for next-generation photoresists. Photoresist materials, when synthesized using sulfonylaminoethyl α-substituted acrylates as photoresist monomers, are provided with excellent light transparency and surface adsorptivity as reported in U.S. Pat. No. 6,165,678 (hereinafter referred to as "Patent Document 1"). In Patent Document 1, however, there is no detailed description about the synthesis of a fluorine-containing alkylsulfonylaminoethyl α-substituted acrylate represented by the formula [3], which is a target compound of the present invention. Patent Document 1 merely discloses a process for synthesizing a sulfonylaminoethyl α-substituted acrylate in a broad sense by condensation of the corresponding sulfonylaminoethanol with α-substituted acryloyl chloride. It is further reported in Japanese Laid-Open Patent Publication 2005-281301 (hereinafter referred to as "Patent Document 2") that the synthesis process of Patent Document 1 is not suitable for the synthesis of a fluorine-containing alkylsulfonylaminoethyl α-substituted acrylate.

As a solution to the above problem, Patent Document 2 proposes a process for synthesizing a fluorine-containing alkylsulfonylaminoethyl α-substituted acrylate of the formula [3] by reacting an aminoethyl α-substituted acrylate or salt thereof with a fluorine-containing alkylsulfonic halide or fluorine-containing alkylsulfonic anhydride, as indicated in the following scheme, using acetonitrile as a reaction solvent.

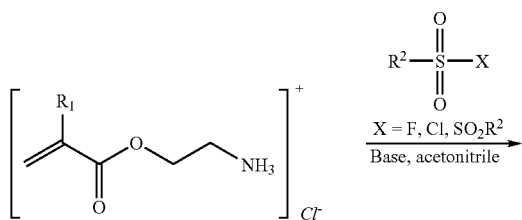

Further, U.S. Pat. No. 6,949,325 (hereinafter referred to as "Patent Document 3") proposes a process for synthesizing a fluorine-containing alkylsulfonylaminoethyl α-substituted acrylate by reaction of a fluorine-containing alkylsulfonic chloride and an aminoethyl α-substituted acrylate using methylene chloride as a reaction solvent as indicated in the following scheme.

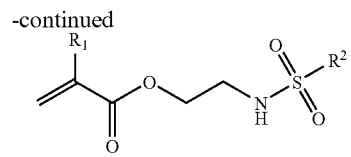

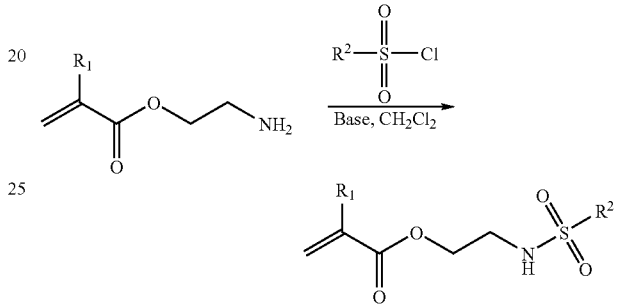

SUMMARY OF THE INVENTION

The synthesis processes of Patent Document 2 and Patent document 3 present the following problems.

The synthesis process of Patent Document 3 utilizes methylene chloride as the reaction solvent. The methylene chloride is known as a beneficial solvent for allowing a reaction to proceed even under moderate temperature conditions, but has to be handled in a closed reaction system because of its toxic properties. The massive use of such a toxic solvent becomes a burden on industrial production of the target compound.

The synthesis process of Patent Document 2 utilizes acetonitrile as the reaction solvent. The acetonitrile is easily available and easy-to-handle. Further, it has been shown that the synthetics process of Patent Document 2 provides a particularly high yield of the target compound by the use of a fluorine-containing alkylsulfonic fluoride as the reaction substrate, which is easily available in large quantity. The synthesis process of Patent Document 2 however requires strong cooling conditions of −30 to −50° C. It is very costly to keep a high-volume reactor cooled to −30° C. in terms of equipment and refrigerant. The strong cooling of the high-volume reactor becomes a burden on industrial mass-production of the target compound. Although it is desirable that the reaction proceeds at around 0° C. for advantageous industrial production, the synthesis process of Patent Document 2 results in a much lower production yield at around 0° C. than at −30° C. or lower. (See Comparative Example 1.) The content of the target compound in the reaction mixture thus decreases to increase the burden of purification of the target compound.

In view of the above prior art problems, there is a need to develop a process for synthesizing a fluorine-containing alkylsulfonylaminoethyl α-substituted acrylate efficiently even under moderate conditions (higher temperature conditions) for easy, cost-effective industrial production.

It is therefore an object of the present invention to provide an industrially advantageous process for producing a fluorine-containing alkylsulfonylaminoethyl α-substituted acrylate.

As a result of extensive researches, the present inventors have found that the use of a fluorine-containing compound as a reaction solvent allows a significant increase in reactivity between a salt of an aminoethyl α-substituted acrylate or an α-substituted acrylate of the formula [1a], which can be prepared by neutralizing an α-substituted acrylate salt with a base, and a fluorine-containing alkylsulfonic fluoride of the formula [2] and leads to a high production yield of target fluorine-containing alkylsulfonylaminoethyl α-substituted acrylate of the formula [3] without low temperature cooling to −30 to −50° C.:

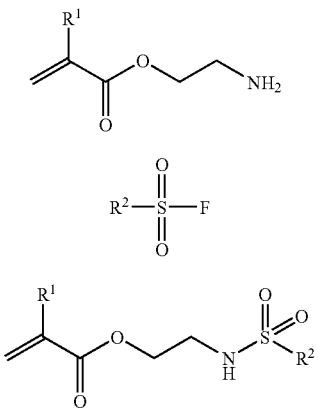

where $R^1$ is a hydrogen atom, methyl group, ethyl group, n-propyl group, isopropyl group, n-butyl group, sec-butyl group, tert-butyl group, fluoromethyl group, difluoromethyl group, trifluoromethyl group or perfluoroethyl group; and $R^2$ is a fluorine-containing alkyl group having a carbon number of 1 to 6. The present invention is based on the above finding.

According to an aspect of the present invention, there is provided a process for producing a fluorine-containing alkylsulfonylaminoethyl α-substituted acrylate of the formula [3] by reacting an aminoethyl α-substituted acrylate represented by the formula [1a] with a fluorine-containing alkylsulfonic fluoride represented by the formula [2] or by reacting a salt of aminoethyl α-substituted acrylate represented by the formula [1b] with a fluorine-containing alkylsulfonic fluoride represented by the formula [2] in the presence of a base, wherein a fluorine-containing compound is used as a reaction solvent:

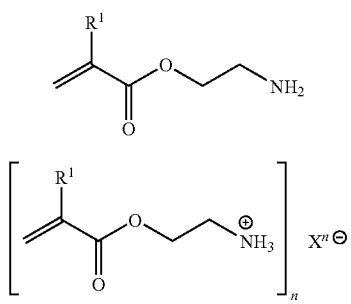

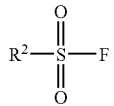

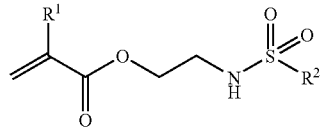

where $R^1$ is a hydrogen atom, methyl group, ethyl group, n-propyl group, isopropyl group, n-butyl group, sec-butyl group, tert-butyl group, fluoromethyl group, difluoromethyl group, trifluoromethyl group or perfluoroethyl group; $R^2$ is a fluorine-containing alkyl group having a carbon number of 1 to 6; $X^{n-}$ is a counter anion (n is a positive integer); and Y is a fluorine atom, chlorine atom or bromine atom.

DETAILED DESCRIPTION OF THE INVENTION

The present invention will be described in more detail below.

In the present invention, the fluorine-containing alkylsulfonylaminoethyl α-substituted acrylate of the formula [3] is produced by sulfonamidation reaction between the aminoethyl α-substituted acrylate of the formula [1a] and the fluorine-containing alkylsulfonic fluoride of the formula [2], or by sulfonamidation reaction between the aminoethyl α-substituted acrylate salt of the formula [1b] and the fluorine-containing alkylsulfonic fluoride of the formula [2] in the presence of a base, using the fluorine-containing compound as the reaction solvent. It is possible to accelerate the sulfonamidation reaction of the aminoethyl α-substituted acrylate [1a] or aminoethyl α-substituted acrylate salt [1b] and the fluorine-containing alkylsulfonic fluoride [2] by the use of the fluorine-containing compound as the reaction solvent. Thus, the production process of the present invention provides a much higher yield of the fluorine-containing alkylsulfonylaminoethyl α-substituted acrylate [3] than conventional production processes even under moderate temperature conditions and can be advantageously applied to the industrial production of the fluorine-containing alkylsulfonylaminoethyl α-substituted acrylate [3].

In the target fluorine-containing alkylsulfonylaminoethyl α-substituted acrylate [3], the substituent $R^1$ is a hydrogen atom, methyl group, ethyl group, n-propyl group, isopropyl group, n-butyl group, sec-butyl group, tertbutyl group, fluoromethyl group, difluoromethyl group, trifluoromethyl group or perfluoroethyl group whereas the substituent $R^2$ is a fluorine-containing $C_1$-$C_6$ alkyl group, preferably fluoromethyl group, difluoromethyl group, perfluoroethyl group, n-perfluoropropyl group or n-perfluorobutyl group. The reaction substrates [1a], [1b] and [2] can be thus selected appropriately depending on the substituents $R^1$ and $R^2$ of the target reaction product [3]. In view of the usability of the reaction product [3], it is preferable that the substituent $R^1$ is methyl and the substituent $R^2$ is trifluoromethyl.

There is no particular restriction on the counter anion $X^{n-}$ of the aminoethyl α-substituted acrylate salt [1b] as long as the counter anion $X^{n-}$ is an inert ion that does not affect the reaction between the aminoethyl α-substituted acrylate salt [1b] and the fluorine-containing alkylsulfonic fluoride [2].

The counter anion $X^{n-}$ is preferably a monovalent anion, divalent anion or trivalent anion (i.e. n is an integer of 1, 2 or 3). Examples of the counter anion $X^{n-}$ are fluoride ion, chloride ion, bromide ion, iodide ion, perchlorate ion, perbromate ion, bisulfate ion (hydrogen sulfate ion), sulfate ion and phosphate ion.

The aminoethyl α-substituted acrylate [1a] and the aminoethyl α-substituted acrylate salt [1b] may be prepared in the same manner as disclosed in Patent Document 2. More specifically, the aminoethyl α-substituted acrylate salt [1b] can be prepared by adding a carboxylic chloride such as methacrylic chloride to a hydrochloride of aminoethanol. The aminoethyl α-substituted acrylate [1a] can be prepared by treating the above-prepared aminoethyl α-substituted acrylate salt [1b] with a base. On the other hand, the fluorine-containing alkylsulfonic fluoride [2] can be prepared by electrolytic fluorination of the corresponding alkylsulfonic fluoride in the same manner as disclosed in "Fluorine Chemistry", p. 75-76 (published by Kodansha Scientific Ltd. in 1979).

In the present invention, the reaction can be carried out in a batch-type reactor under the following conditions. The reaction conditions are not limited thereto and may be modified as appropriate within the general knowledge of any person skilled in the art.

It is preferable to carry out the reaction between the aminoethyl α-substituted acrylate [1a] and the fluorine-containing alkylsulfonic fluoride [2] in the presence of a base for higher production yield although the free aminoethyl α-substituted acrylate [1a] reacts with the fluorine-containing alkylsulfonic fluoride [2] even without the base. On the other hand, it is essential to carry out the reaction between the aminoethyl α-substituted acrylate salt [1b] and the fluorine-containing alkylsulfonic fluoride [2] in the presence of the base.

For both of the reaction between the aminoethyl α-substituted acrylate [1a] and the fluorine-containing alkylsulfonic fluoride [2] and the reaction between the aminoethyl α-substituted acrylate salt [1b] and the fluorine-containing alkylsulfonic fluoride [2], the base is preferably at least one selected from the group consisting of: trimethylamine; triethylamine; N,N-diethylmethylamine; tripropylamine; tributylamine; pyridine; 2,6-dimethylpyridine; N,N-dimethylaminopyridine; sodium carbonate; potassium carbonate; sodium hydroxide; and potassium hydroxide. Especially preferred is triethylamine because of its high reactivity.

As the base, a protic base such as ammonia, primary amine or secondary amine is usable. However, there is a possibility that the protic base reacts with the fluorine-containing alkylsufonic fluoride [2] to form the corresponding amine and cause a decrease in production yield. The protic base is thus less preferred.

In the case of using the aminoethyl α-substituted acrylate [1a] as the reaction substrate, the base is used in an amount of generally 0.2 to 15.0 mol, preferably 0.5 to 10.0 mol, more preferably 1.0 to 3.0 mol, per 1.0 mol of the aminoethyl α-substituted acrylate [1a]. When the amount of the base is less than 0.2 mol per 1.0 mol of the aminoethyl α-substituted acrylate [1a], the selectivity and yield of the reaction becomes lowered. When the amount of the base exceeds 15.0 mol per 1.0 mol of the aminoethyl α-substituted acrylate [1a], the amount of remaining unreacted base becomes increased. The addition of such an excessive base is economically undesirable. It is alternatively conceivable to use an excessive amount of cheaply-available triethylamine as the base so that the remaining unreacted triethylamine functions as a fluorine-free solvent as will be described later. In this case, the triethylamine may be used in an amount exceeding 15 mol.

In the case of using the aminoethyl α-substituted acrylate salt [1b] as the reactant material, the base is used in an amount of generally 0.5 to 30.0 mol, preferably 0.8 to 15.0 mol, more preferably 1.5 to 5.0 mol, per 1.0 mol of the aminoethyl α-substituted acrylate salt [1b]. When the amount of the base is less than 0.5 mol per 1.0 mol of the aminoethyl α-substituted acrylate salt [1b], the selectivity and yield of the reaction becomes lowered. If the amount of the base exceeds 30.0 mol per 1.0 mol of the aminoethyl α-substituted acrylate salt [1b], the amount of remaining unreacted base becomes increased. The addition of such an excessive base is economically undesirable. It is alternatively conceivable to use an excessive amount of cheaply-available triethylamine as the base so that the remaining unreacted triethylamine functions as a fluorine-free solvent as will be described later. In this case, the triethylamine may be used in an amount exceeding 30 mol.

The amount of the fluorine-containing alkylsulfonic fluoride [2] is generally 0.2 to 3.0 mol, preferably 0.5 to 1.5 mol, more preferably 0.9 to 1.2 mol, per 1.0 mol of the aminoethyl α-substituted acrylate [1a] or aminoethyl α-substituted acrylate salt [1b]. When the amount of the fluorine-containing alkylsulfonic fluoride [2] is less than 0.2 mol per 1.0 mol of the aminoethyl α-substituted acrylate [1a] or aminoethyl α-substituted acrylate salt [1b], the selectivity and yield of the reaction becomes lowered. When the amount of the fluorine-containing alkylsulfonic fluoride [2] exceeds 3.0 mol per 1.0 mol of the aminoethyl α-substituted acrylate [1a] or aminoethyl o-substituted acrylate salt [1b], the amount of remaining unreacted fluorine-containing alkylsulfonic fluoride becomes increased. It is economically undesirable to use such an excessive reaction substrate in view of efforts and costs for disposal of the unreacted reaction substrate. The production process of the present invention is advantageous in that the reaction proceeds smoothly without the need to use a large excess of any one reaction substrate. In order to take such an advantage, it is particularly preferable to control the amount of the fluorine-containing alkylsulfonic fluoride [2] in such a manner that the mole ratio between the aminoethyl α-substituted acrylate [1a] or aminoethyl α-substituted acrylate salt [1b] and the fluorine-containing alkylsulfonic fluoride [2] is equal or close to 1:1.

Further, the present invention is characterized in that the fluorine-containing compound is used as the reaction solvent as described above. There is no particular restriction on the fluorine-containing compound. The fluorine-containing compound can be any generally recognized fluorine-containing solvent.

Preferably, the fluorine-containing compound has one or more trifluoromethyl groups in terms of its availability and stability.

The fluorine-containing compound is preferably at least one selected from the group consisting of: chlorofluorocarbon compounds such as 1,1,2-trichloro-2,2-difluoroethane, 1,1-dichloro-2,2-difluoroethane, 1,1,2-trichloro-2-fluoroethane, 1,1-dichloro-2,2,3,3,3-pentafluoropropane and 1,1,1,3,3-pentafluorobutane; fluorine-containing ether compounds such as 2-chloro-1,1,2-trifluoroethyl ethyl ether, 2chloro-1,1,2-trifluoroethyl methyl ether, ethyl 1,1,2,2-tetrafluoroethyl ether, 1,1,3,3,3-pentafluoropropyl methyl ether, heptafluoropropyl 1,2,2,2-tetrafluoroethyl ether, 1,1,1,2,3,3-hexafluoropropyl methyl ether, 1,1,1,2,3,3-hexafluoropropyl 2,2,2-trifluoroethyl ether, 1-(methoxy)nonafluorobutane and 1-(ethoxy)nonafluorobutane; fluorine-containing ester compounds such as methyl trifluoroacetate, ethyl trifluoroacetate, n-butyl trifluoroacetate, methyl pentafluoropropionate, ethyl pentafluoropropionate, methyl perfluoropentanoate, ethyl perfluoropentanoate, methyl perfluoroheptanoate, ethyl perfluoroheptanoate, methyl perfluorooctanoate, ethyl perfluorooctanoate, methyl perfluorononanoate, ethyl perfluorononanoate, methyl 2,3,3,3-tetrafluoropropionate, ethyl 2,3,3,3-tetrafluoropropionate, 2,2,2-trifluoromethyl acetate and 2,2,2-trifluoromethyl butanoate; fluorine-containing aromatic compounds such as trifluoromethyl benzene, m-bis(trifluoromethyl)benzene, p-bis(trifluoromethyl)benzene, 2,4-dichlorobenzotrifluoride, fluorobenzene, 1,2-difluorobenzene, 1,3-difluorobenzene, 1,4-difluorobenzene, 1,2,4-trifluorobenzene, pentafluorobenzene, hexafluorobenzene, 2-fluorotoluene, 3-fluorotoluene and 4-fluorotoluene; fluorine-containing cycloalkane compounds such as 1,2-dichlorohexafluorocyclobutane, perfluorodimethylcyclobutane, 1,2-dichlorohexafluorocyclopenta-1-ene, 1,1,2,2,3,3,4-heptafluorocyclopentane, octafluorocyclopentane, perfluoromethylcyclohexane, perfluoro-1,2-dimethylcyclohexane, perfluoro-1,3-dimethylcyclohexane and perfluoroethyl dimethyl cyclohexane; perfluoroalkane compounds represented by the following formula: $CF_3(CF_2)_xCF_3$ (where x is an integer of 4 to 20, preferably 4 to 10); and perfluoroalkylamine compounds represented by the following formula: $N\{(CF_2)_yCF_3\}_3$ (where y is an integer of 1 to 20, preferably 2 to 5).

Among others, 1,1,2,2,3,3,4-heptaflurocyclopentane, trifluoromethyl benzene, 1,3-bis(trifluoromethyl) benzene and 1,4-bis(trifluoromethyl) benzene are particularly preferred. These fluorine-containing compounds allows a significant increase in production yield under moderate temperature conditions e.g. at around 0° C. to room temperature. (It is noted that the term "room temperature" generally refers to 25° C. throughout the present specification.)

It is less preferable to use a protic fluorine-containing compound such as fluorinated alcohol as the reaction solvent because the protic fluorine-containing compound may react with the fluorine-containing alkylsulfonic fluoride [2] to form the corresponding sulfonic ester and causes a decrease in production yield.

In the present invention, the reaction proceeds favorably even when the fluorine-containing compound is used solely as the reaction solvent. In view of the facts that the reaction substrate (aminoethyl α-substituted acrylate salt) [1b] is solid; and the precipitation of a halogen acid salt of the base occurs as a by-product of the reaction, however, there may be a burden on process operations such as stirring and solution transfer due to the difficulty of uniform dispersion of these solid materials in the reaction solution by the use of the fluorine-containing compound solely as the reaction solvent.

On this account, a fluorine-free compound may preferably coexist with the fluorine-containing compound so as to use a mixed solvent of the fluorine-containing compound and the fluorine-free compound as the reaction solvent. The coexistence of the fluorine-free compound with the fluorine-containing compound allows a significant increase in operation efficiency without loss of the reactivity improvement effect of the fluorine-containing compound.

Examples of the fluorine-free solvent are: nitrite solvents such as acetonitrile and benzonitrile; amide solvents such as N,N-dimethylformamide, N,N-dimethylacetamide and N,N-dimethyl-imidazolydinone; sulfoxide solvents such as dimethyl sulfoxide; ether solvents such as diethyl ether, diisopropyl ether, dibutyl ether and tetrahydrofuran; basic solvents such as triethylamine, trimethylamine, tripropylamine, tributylamine and pyridine; halogenated solvents such as methylene chloride, chloroform (trichloromethane) and carbon tetrachloride (tetrachloromethane); aromatic hydrocarbon solvents such as benzene, toluene and xylene; pentane; hexane; heptane; and any combination thereof.

It is less preferable to use a protic fluorine-free solvent such as water, alcohol, ammonia and primary and secondary amines because the protic fluorine-free compound may react with the fluorine-containing alkylsulfonic fluoride [2] to form the corresponding sulfonic ester and causes a decrease in production yield.

Among others, the fluorine-free compound is preferably at least one selected from the group consisting of: nitrite solvents such as acetonitrile and benzonitrile; amide solvents such as N,N-dimethylformamide, N,N-dimethylacetamide and N,N-dimethyl-imidazolydinone; sulfoxide solvents such as dimethyl sulfoxide; ether solvents such as diethyl ether, diisopropyl ether, dibutyl ether and tetrahydrofuran; and basic solvents such as triethylamine and pyridine for greater operation efficiency improvement and less environmental impacts.

In the case of adding the liquid base such as trimethylamine, triethylamine, N,N-diethylmethylamine, tripropylamine, tributylamine, pyridine, 2,6-dimethylpyridine or N,N-dimethylaminopyridine in an amount exceeding the minimum base amount (equivalent weight) required for the reaction (i.e. equal to the mole number of the reaction substrate in the case where the aminoethyl α-substituted acrylate [1a] is used as the reaction substrate; and twice the molar amount of the reaction substrate in the case where the aminoethyl α-substituted acrylate salt [1b] is used as the reaction substrate), the base also functions as the fluorine-free solvent compound.

In the case of using the mixed solvent of the fluorine-containing compound and the fluorine-free compound as the reactions solvent, the proportion of the fluorine-containing compound in the mixed solvent is generally 5 to 80%, preferably 20 to 70%, more preferably 30 to 60%. When the proportion of the fluorine-containing compound in the mixed solvent is less than 5%, the reactivity improvement effect of the fluorine-containing compound becomes insufficient. On the other hand, when the proportion of the fluorine-containing compound in the mixed solvent exceeds 80%, the operation efficiency improvement effect of the fluorine-free compound becomes insufficient.

The amount of the fluorine-containing compound as the reaction solvent is generally 0.05 to 20 g, preferably 0.5 to 10 g, more preferably 2 to 5 g, per 1 g of the aminoethyl α-substituted acrylate [1a] or aminoethyl α-substituted acrylate salt [1b]. The reactivity improvement effect of the fluorine-containing compound becomes insufficient when the amount of the fluorine-containing compound is less than 0.05 g. It is economically undesirable to use the fluorine-containing compound in an amount exceeding 20 g in terms of productivity.

There is no particular restriction on the temperature of the reaction. As the production process of the present invention is advantageous in that the target compound [3] can be obtained with a high yield even at a temperature higher than −30° C. by the use of the fluorine-containing compound as the reaction solvent, the reaction temperature is generally controlled to −25 to 50° C., preferably −20 to 30° C., more preferably −10° C. to room temperature (25° C.). It is particularly preferable to control the reaction temperature to −10 to 20° C. in the initial stage of the reaction. Although the reaction proceeds favorably even at a temperature of −30° C. or lower, it is industrially undesirable to control the reaction temperature to such an extremely low level in view of cooling cost as described above. When the reaction temperature exceeds 50° C., there arises an undesirable tendency that the reaction substrate (aminoethyl α-substituted acrylate [1a] or aminoethyl α-substituted acrylate salt [1b]) or the reaction product (fluorine-containing alkylsulfonylaminoethyl a-substituted acrylate [3]) will be polymerized.

There is no particular restriction on the reactor as long as the reactor is durable under the reaction conditions. The reactor is preferably made with a lining of tetrafluoroethylene resin, chlorotrifluoroethylene resin, fluorovinylidene resin, PFA (perfluoroalkoxy) resin or glass, or made of glass or stainless steel.

Although the reaction can be carried out in an inert gas atmosphere, there is no significant difference of reactivity under the inert gas atmosphere and in the air. It is thus preferable to carry out the reaction in the air in terms of cost for industrial mass-production.

In the present invention, the sulfonamidation reaction may be interfered with by water or protic compound when the water or protic compound is undesirably mixed into the reaction system. In order to prevent such a reaction interference problem, it is preferable to dehydrate the fluorine-containing compound and the fluorine-free compound used as the reaction solvent. The permissible content of the water or protic compound in the reaction solvent varies depending on the amount of the reaction solvent and is preferably 0.3% or lower, more preferably 0.05% or lower.

As the production process of the present invention does not require pressurized conditions, the reactor can be either an atmospheric reactor or a pressure reactor. There is almost no production yield improvement seen when the reaction proceeds under pressurized conditions. It would be however advantageous to carry out the reaction in a closed reaction system by the use of the pressure reactor for ease of reaction control for mass-production.

For example, the production process of the present invention can be performed by the following procedure.

The base, the reaction solvent, the aminoethyl α-substituted acrylate salt [1b] as the reaction substrate are placed, together with a polymerization inhibitor, into the reactor. The resulting reaction mixture is cooled by a refrigerant with stirring. After the reaction mixture reaches a constant temperature, a predetermined amount of fluorine-containing alkylsulfonic fluoride is added into the reaction mixture. It is herein preferable to confirm the completion of the reaction by monitoring the formation of the target compound (more specifically, the end of increase of the formation amount of the target compound) through sampling or the like.

The time of the reaction cannot be categorically determined as the reactivity varies depending on the kinds of the base, solvent and reactants. The reaction time is usually 0.5 to 12 hours, preferably 1 to 6 hours, more preferably 2 to 4 hours. When the reaction time is less than 0.5 hour, the reaction is still in progress at the end of the reaction time. The yield of the reaction becomes lowered by stopping the reaction in progress. When the reaction time exceeds 12 hours, the reaction is completed during the reaction time. No yield improvement effect would be provided by continuing the reaction for such a long reaction time. There will be no problem even when the reaction is continued for over 12 hours for operational reasons such as time schedule After the completion of the reaction, the fluorine-containing alkylsulfonylaminoethyl α-substituted acrylate [3] is purified by any known purification operation. For example, the fluorine-containing alkylsulfonylaminoethyl α-substituted acrylate [3] can be obtained as a crude reaction product by evaporating the reaction solvent under reduced pressure, suspending the evaporated residue in any suspension medium such as diisopropylether, filtrating the precipitated halogen acid salt of the base, and evaporating the suspension medium.

The crude reaction product is further purified by column chromatography, distillation and/or recrystallization. In this way, the fluorine-containing alkylsulfonylaminoethyl α-substituted acrylate is obtained with high purity.

The present invention will be described in more detail by reference to the following examples. It should be however noted that the following examples are only illustrative and not intended to limit the invention thereto. In the following explanation, the unit "%" of composition analysis values means "area %" of organic components excluding solvent components, each obtained by sampling a part of the reaction mixture or reaction product, dissolving the organic component into diisopropyl ether, and measuring the solution by gas chromatography.

EXAMPLE 1

In a 2-liter three-neck flask equipped with a thermometer, a reflex condenser and a calcium chloride tube were placed 200 g of acetonitrile, 200g of 1,1,2,2,3,3,4-heptafluorocyclopentane (HFCPA), 134.7 g (1.33 mol) of triethylamine and 100.0 g (0.6 mol) of 2-aminoethyl 2-methylacrylate hydrochloride, followed by cooling to 0° C. with stirring. After the inside temperature of the flask reached 0° C., 101.3 g (0.66 mol) of trifluoromethanesulfonyl fluoride was introduced as a gas into the slurry. The flask inside temperature was kept below 10° C. during the gas introduction. Upon completion of the gas introduction, the reaction solution was warmed to room temperature with stirring. To the reaction solution was added 300 g of clean water. The solution was stirred for 30 minutes, and then, separated into two phases: an aqueous phase and an organic phase. After removal of the aqueous phase, a diluted aqueous sulfuric acid solution (obtained by mixing 10 g of sulfuric acid and 300 g of clean water) was added to the organic phase. The resulting solution was further stirred for 30 minutes and subjected to two-phase separation. The same washing operation was repeated using a sodium bicarbonate solution (obtained by mixing 10 g of sodium acid carbonate and 300 g of clean water). The solvent was evaporated under a reduced pressure to obtain a crude reaction product. The crude reaction product was dissolved into a mixed solvent of isopropyl ether and heptane under heating. The reaction product was crystallized from the solution by cooling, filtered out and then dried, thereby collecting 111 g of target 2-{[(trifluoromethyl)sulfonyl]amino}ethyl 2-methylacrylate. The purity of the 2-{[(trifluoromethyl)sulfonyl] amino}ethyl 2-methylacrylate was determined by gas chromatography to be 98.0%. The yield of the 2-{ [(trifluoromethyl)sulfonyl]amino}ethyl 2-methylacrylate was 71%.

Melting point: 47 to 48° C.

$^1$H NMR (solvent: CDCl$_3$, standard substance: TMS): δ 6.16 (dq, J=0.98 Hz, J=1.22 Hz, 1H), 5.66 (dq, J=1.46 Hz, J=1.22 Hz, 1H), 4.32 (dd, J=5.12 Hz, J=1.71 Hz, 2H), 3.61 (dt, J=0.49 Hz, J=5.12 Hz, 2H), 1.96 (dd, J=0.98 Hz, J=1.46 Hz, 3H)

$^{19}$F NMR (solvent: CDCl$_3$, standard substance: TMS): δ −77.79 (s, 3F)

In Example 1, the target compound was produced with a favorably high yield even at temperatures of 0° C. or higher through the use of the mixed reaction solvent of HFCPA as the fluorine-containing compound and acetonitrile as the fluorine-free compound as explained above. The operability of the reaction solution was also good during and after the reaction.

EXAMPLE 2

In a 2-liter three-neck flask equipped with a thermometer, a reflex condenser and a calcium chloride tube were placed 300 g of HFCPA, 134.7 g (1.33 mol) of triethylamine and 100.0 g (0.6 mol) of 2-aminoethyl 2-methylacrylate hydrochloride, followed by cooling to 0° C. with stirring. After the inside temperature of the flask reached 0° C., 101.3 g (0.66 mol) of trifluoromethanesulfonyl fluoride was introduced as a gas into the slurry. The flask inside temperature was kept below 10° C. during the gas introduction. Upon completion of the gas introduction, the reaction solution was warmed to room temperature with stirring. To the reaction solution was added 300 g of clean water. The solution was stirred for 30 minutes, and then, subjected to two-phase separation. After removal of the aqueous phase, a diluted aqueous sulfuric acid solution (obtained by mixing 10 g of sulfuric acid and 300 g of clean water) was added to the organic phase. The resulting solution was further stirred for 30 minutes and subjected to two-phase separation. The same washing operation was repeated using a sodium bicarbonate solution (obtained by mixing 10 g of sodium acid carbonate and 300 g of clean water). The solvent was evaporated under a reduced pressure to obtain a crude reaction product. The crude reaction product was dissolved into a mixed solvent of isopropyl ether and heptane under heating. The reaction product was crystallized from the solution by cooling, filtered out and then dried, thereby collecting 102 g of target 2-{[(trifluoromethyl)sulfonyl]amino}ethyl 2-methylacrylate. The purity of the 2-{[(trifluoromethyl)sulfonyl]amino}ethyl 2-methylacrylate was determined by gas chromatography to be 97.8%. The yield of the 2-{[(trifluoromethyl)sulfonyl]amino}ethyl 2-methylacrylate was 65%.

In Example 2, the target compound was also produced with a favorably high yield even at temperatures of 0° C. or higher through the use of the fluorine-containing compound solely as the reaction solvent.

EXAMPLES 3 TO 6

The production of 2-{[(trifluoromethyl)sulfonyl]amino}ethyl 2-methylacrylate was conducted under the same conditions as those of Example 1, except for the reaction temperature and solvent as listed in TABLE. In Examples 3 to 6, the target compound was produced with a favorably high yield of 66 to 74% even at temperatures of 0° C. or higher by the selection of the reaction solvent among various fluorine-containing compounds.

COMPARATIVE EXAMPLE 1

(Reaction in Fluorine-Free Solvent)

In a 2-liter three-neck flask equipped with a thermometer, a reflex condenser and a calcium chloride tube were placed 200 g of acetonitrile, 200 g of disopropyl ether, 134.7 g (1.33 mol) of triethylamine and 100.0 g (0.6 mol) of 2-aminoethyl 2-methylacrylate hydrochloride, followed by cooling to 0° C. with stirring. After the inside temperature of the flask reached 0° C., 101 g (0.66 mol) of trifluoromethanesulfonyl fluoride was introduced as a gas into the slurry over 1 hour. Upon completion of the gas introduction, the reaction solution was warmed to room temperature with stirring. To the reaction solution was added 300 g of clean water. The solution was stirred for 30 minutes, and then, subjected to two-phase separation. After removal of the aqueous phase, a diluted aqueous sulfuric acid solution (obtained by mixing 10 g of sulfuric acid and 300 g of clean water) was added to the organic phase. The resulting solution was further stirred for 30 minutes and subjected to two-phase separation. The same washing operation was repeated, after removal of the aqueous phase, using a sodium bicarbonate solution (obtained by mixing 10 g of sodium acid carbonate and 300 g of clean water). The solvent was evaporated under a reduced pressure to obtain a crude reaction product. The crude reaction product was dissolved into a mixed solvent of isopropyl ether and heptane under heating. The reaction product was crystallized from the solution by cooling, filtered out and then dried, thereby collecting 65.7 g of 2-{[(trifluoromethyl)sulfonyl]amino}ethyl 2-methylacrylate with high purity. The yield of the 2-{[(trifluoromethyl)sulfonyl]amino}ethyl 2-methylacrylate was 42%.

In Comparative Example 1, the reaction was carried out at temperatures from 0° C. to room temperature using a fluorine-free mixed solvent of acetonitrile and diisopropyl ether. As a result, the yield of Comparative Example 1 was significantly decreased relative to that of Reference Example 1 (where the reaction was conducted at −30° C. as will be described later) and was much lower than those of Examples 1 to 6.

COMPARATIVE EXAMPLE 2

(Reaction in Fluorine-Free Solvent Under Pressurized Conditions)

In a 1-liter autoclave equipped with a thermometer, a gas flow tube and an agitator were placed 100 g of acetonitrile, 300 g of isopropyl ether (IPE), 134.6 g (1.33 mol) of triethylamine and 100.0 g (0.6 mol) of 2-aminoethyl 2-methylacrylate hydrochloride, followed by cooling to 0° C. with stirring. After the inside temperature of the autoclave reached 0° C., 101.3 g (0.66 mol) of trifluoromethanesulfonyl fluoride was introduced as a gas through the gas flow tube over 1 hour. During the gas introduction, the reaction temperature rose to 5° C. by heat generation. The maximum pressure was 0.05MPa. Upon completion of the gas introduction, the reaction solution was warmed to room temperature with stirring over 30 minutes. The reaction solution was further stirred for 3 hours. At this time, the pressure was 0.02 MPa. The reaction mixture was taken out of the autoclave after release of the residual pressure of trifluoromethanesulfonyl fluoride. To the reaction mixture was added 300 g of clean water. The solution was stirred for 30 minutes, and then, subjected to two-phase separation. After removal of the aqueous phase, a diluted aqueous sulfuric acid solution (obtained by mixing 10 g of sulfuric acid and 300 g of clean water) was added to the organic phase. The resulting solution was further stirred for 30 minutes and subjected to two-phase separation. The same washing operation was repeated, after removal of the aqueous phase, using a sodium bicarbonate solution (obtained by mixing 10 g of sodium acid carbonate and 300 g of clean water). The solvent was evaporated under a reduced pressure to obtain a crude reaction product. The crude reaction product was dissolved into a mixed solvent of isopropyl ether and heptane under heating. The reaction product was crystallized from the solution by cooling, filtered out and then dried, thereby collecting 67 g of 2-{[(trifluoromethyl)sulfonyl]amino}ethyl 2-methylacrylate. The purity of the 2-{[(trifluoromethyl)sulfonyl]amino}ethyl 2-methylacrylate was determined by gas chromatography to be 99.0%. The yield of the 2-{[(trifluoromethyl)sulfonyl]amino}ethyl 2-methylacrylate was 43%.

In Comparative Example 2, the reaction was carried out under pressurized conditions in a closed system within the autoclave (reactor) at temperatures of 0° C. or higher using a fluorine-free mixed solvent of acetonitrile and isopropyl ether. There was no significant improvement seen between the yield of the reaction under normal pressure conditions in Comparative Example 1 and the yield of the reaction under pressurized conditions in Comparative Example 2. The yield of Comparative Example 2 was much lower than those of Examples 1 to 6.

REFERENCE EXAMPLE 1

(Reaction in Acetonitrile Solvent Under Strong Cooling Conditions)

In a 1-liter three-neck flask equipped with a thermometer, a reflex condenser and a calcium chloride tube were placed 350 g of acetonitrile, 70.7 g (0.699 mol) of triethylamine, 33.1 g (0.200 mol) of 2-aminoethyl 2-methylacrylate hydrochloride and 0.2 g of phenothiazine as a polymerization inhibitor, followed by cooling to −30° C. with stirring. After the inside temperature of the flask reached −30° C. C, 36.5 g (0.240 mol) of trifluoromethanesulfonyl fluoride was introduced as a gas into the slurry over 1 hour. Upon completion of the gas introduction, the reaction solution was stirred for 1 hour and then warmed to room temperature. The solvent (acetonitrile) and the unreacted reaction substrate (trifluoromethanesulfonyl fluoride) were evaporated from the reaction solution under a reduced pressure. To the solution was added 1 liter of diisopropyl ether. The resulting slurry was subjected to filtration to filter out precipitates of triethylamine hydrochloride and triethylamine hydrofluoride. The filtrate was washed with 200 ml of 18% aqueous calcium chloride solution and subjected to two-phase separation. The organic phase was further washed three times with 200 g of 10% aqueous sodium chloride solution, and then, dried with 40 g of magnesium sulfate. The magnesium sulfate was removed by filtration. After that, 0.2 g of phenothiazine was added to the organic phase. The solvent was evaporated to obtain 44.2 g of a crude reaction product. The crude reaction product was subjected to distillation under a reduced pressure, thereby yielding 36.0 g of target 2-{[(trifluoromethyl)sulfonyl]amino}ethyl 2-methylacrylate as an organic fraction at 105-115° C./13Pa. The purity of the 2-{[(trifluoromethyl)sulfonyl]amino}ethyl 2-methylacrylate in the organic fraction was determined by gas chromatography to be 97.0%. The organic fraction was dissolved into a mixed solvent of diisopropyl ether and n-hexane under heating. The solution was cooled, thereby collecting 32.4 g of the 2-{[(trifluoromethyl)sulfonyl]amino}ethyl 2-methylacrylate as a white crystal. The purity of the 2-{[(trifluoromethyl)sulfonyl]amino}ethyl 2-methylacrylate in the crystal was determined by gas chromatography to be 99.0%. The yield of the 2-{[(trifluoromethyl)sulfonyl]amino}ethyl 2-me thylacrylate was 61%.

In Reference Example 1, the target compound was obtained with a relatively high yield even through the use of acetonitrile as the reaction solvent under strong cooling conditions of −30° C.

REFERENCE EXAMPLE 2

(Reaction in Acetonitrile Solvent Under Strong Cooling Conditions)

In a 1-liter three-neck flask equipped with a thermometer, a reflex condenser and a calcium chloride tube were placed 350 g of acetonitrile, 70.7 g (0.699 mol) of triethylamine, 33.1 g (0.200 mol) of 2-aminoethyl 2-methylacrylate hydrochloride and 0.2 g of phenothiazine, followed by cooling to −30o C with stirring. After the inside temperature of the flask reached −30° C., 40.3 g (0.239 mol) of trifluoromethanesulfonyl chloride was introduced as a gas into the slurry over 1 hour. Upon completion of the gas introduction, the reaction solution was stirred for 1 hour and then warmed to room temperature. The solvent (acetonitrile) and the unreacted reaction substrate (trifluoromethanesulfonyl chloride) were evaporated from the reaction solution under a reduced pressure. To the solution was added 1 liter of diisopropyl ether. The resulting slurry was subjected to filtration to filter out a precipitate of triethylamine hydrochloride. The filtrate was washed three times with 200 g of 10% aqueous sodium chloride solution, and then, dried with 40 g of magnesium sulfate. The magnesium sulfate was removed by filtration. After that, 0.2 g of phenothiazine was added to the organic phase. The solvent was evaporated to obtain 22.5 g of a crude reaction product. The crude reaction product was subjected to distillation under a reduced pressure, thereby yielding 9.9 g of target 2-{[(trifluoromethyl)sulfonyl]amino}ethyl 2-methylacrylate as an organic fraction at 105-115° C. /13Pa. The purity of the 2-{[(trifluoromethyl)sulfonyl]amino}ethyl 2-methylacrylate was determined by gas chromatography to be 98.0%. The yield of the 2-{[(trifluoromethyl)sulfonyl]amino}ethyl 2-methylacrylate was 19%.

In Reference Example 2, the target compound was produced under strong cooling conditions of −30° C. through the use of acetonitrile as the reaction solvent and collected by isolation. The yield of the target compound was low due to the low reactivity of the trifluoromethanesulfonyl chloride reaction substrate.

REFERENCE EXAMPLE 3

(Reaction in Acetonitrile-Methylene Chloride Solvent)

The production of 2-{[(trifluoromethyl)sulfonyl]amino}ethyl 2-methylacrylate was conducted under the same conditions as those of Comparative Example 1 (i.e. at temperatures of 0° C. to room temperature), except for using a mixed solvent of methylene chloride and acetonitrile as the reaction solvent.

In Reference Example 3, the target compound was obtained with a relatively high yield of 61% even at temperatures of 0° C. or higher with the use of methylene chloride as the reaction solvent.

The results of Examples 1 to 6, Comparative Examples 1 and 2 and Reference Examples 1 to 3 are summarized in TABLE.

TABLE

| | Reactant | Temperature | Solvent | Base | Yield |
|---|---|---|---|---|---|
| Example 1 | TfF | 0° C.-RT | HFCPA(200)/acetonitrile(200) | triethylamine | 71% |
| Example 2 | TfF | 0° C.-RT | HFCPA(300) | triethylamine | 65% |
| Example 3 | TfF | 10° C.-RT | HFCPA(200)/acetonitrile(200) | triethylamine | 71% |

TABLE-continued

| | Reactant | Temperature | Solvent | Base | Yield |
|---|---|---|---|---|---|
| Example 4 | TfF | 25° C. | HFCPA(200)/acetonitrile(200) | triethylamine | 66% |
| Example 5 | TfF | 0° C.-RT | BTF(200)/acetonitrile(200) | triethylamine | 74% |
| Example 6 | TfF | 0° C.-RT | MTF-TFM(200)/acetonitrile(200) | triethylamine | 71% |
| Comparative Example 1 | TfF | 0° C.-RT | IPE(200)/acetonitrile(200) | triethylamine | 42% |
| Comparative Example 2 | TfF | 0° C.-RT under pressure | IPE(300)/acetonitrile(100) | triethylamine | 43% |
| Reference Example 1 | TfF | −30° C. | acetonitrile(1057) | triethylamine | 61% |
| Reference Example 2 | TfCl | −30° C. | acetonitrile(1057) | triethylamine | 19% |
| Reference Example 3 | TfF | 0° C. to RT | methylene chloride(200)/acetonitrile(200) | triethylamine | 61% |

Note:
(1) The abbreviations are as follows.
TfF: trifluoromethanesulfonyl fluoride
TfCl: trifluoromethanesulfonyl chloride
HFCPA: 1,1,2,2,3,3,4-heptafluorocyclopentane
BTF: trifluoromethyl benzene
MTF-TFM: 1,3-bis(trifluoromethyl) benzene
IPE: isopropyl ether
RT: room temperature
(2) The value inside the parentheses is in units of "% by weight" relative to the reactant material (2-aminoethyl 2-methylacrylate hydrochloride).

As described above, it is possible to produce the fluorine-containing alkylsulfonylaminoethyl α-substituted acrylate [3] with high yield under more moderate temperature conditions by sulfonamidation reaction between the aminoethyl α-substituted acrylate or salt thereof and the fluorine-containing alkylsulfonic fluoride using the fluorine-containing compound as the reaction solvent.

The entire contents of Japanese Patent Application No. 2007-235143 (filed on Sep. 11, 2007) are herein incorporated by reference.

Although the present invention has been described with reference to the above specific embodiments, the invention is not limited to these exemplary embodiments. Various modification and variation of the embodiments described above will occur to those skilled in the art in light of the above teachings. The scope of the invention is defined with reference to the following claims.

What is claimed is:

1. A process for producing a fluorine-containing alkylsulfonylaminoethyl α-substituted acrylate of the formula [3] by reaction of an aminoethyl α-substituted acrylate of the formula [1a] with a fluorine-containing alkylsulfonic fluoride of the formula [2], or by reaction of an aminoethyl a-substituted acrylate salt of the formula [1b] with a fluorine-containing alkylsulfonic fluoride of the formula [2] in the presence of a base, wherein a fluorine-containing compound is used in combination with a fluorine-free compound as a reaction solvent:

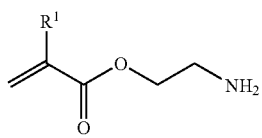

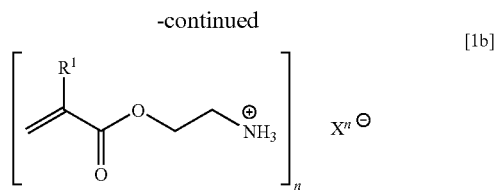

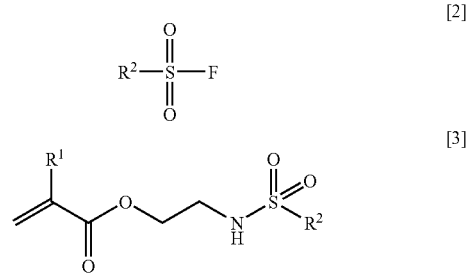

where $R^1$ is a hydrogen atom, methyl group, ethyl group, n-propyl group, isopropyl group, n-butyl group, sec-butyl group, tert-butyl group, fluoromethyl group, difluoromethyl group, trifluoromethyl group or perfluoroethyl group; $R^2$ is a fluorine-containing alkyl group having a carbon number of 1 to 6; and $X^{n-}$ is a counter anion (n is a positive integer).

2. The process according to claim 1, wherein the fluorine-containing compound has one or more trifluoromethyl groups.

3. The process according to claim 1, wherein the fluorine-containing compound is at least one selected from the group consisting of: 1,1,2-trichloro-2,2-difluoroethane; 1,1-dichloro-2,2-difluoroethane; 1,1,2-trichloro-2-fluoroethane; 1,1-dichloro-2,2,3,3,3-pentafluoropropane; 1,1,1,3,3-pentafluorobutane; 2-chloro-1,1,2-trifluoroethyl ethyl ether; 2-chloro-1,1,2-trifluoroethyl methyl ether; ethyl 1,1,2,2-tetrafluoroethyl ether; 1,1,3,3,3-pentafluoropropyl methyl ether; heptafluoropropyl 1,2,2,2-tetrafluoroethyl ether; 1,1,1,2,3,3-hexafluoropropyl methyl ether; 1,1,1,2,3,3-hexafluoropropyl 2,2,2-trifluoroethyl ether; 1-(methoxy)nonafluorobutane; 1-(ethoxy)nonafluorobutane; methyl trifluoroacetate; ethyl trifluoroacetate; n-butyl trifluoroacetate; methyl pentafluoropropionate; ethyl pentafluoropropionate; methyl perfluoropentanoate; ethyl periluoropentanoate; methyl perfluoroheptanoate; ethyl perfluoroheptanoate; methyl perfluorooctanoate; ethyl perfluorooctanoate; methyl perfluorononanoate; ethyl perfluorononanoate; methyl 2,3,3,3-tetrafluoropropionate; ethyl 2,3,3,3-tetrafluoropropionate; 2,2,2-trifluoromethyl acetate; 2,2,2-trifluoromethyl butanoate; trifluoromethyl benzene; m-bis(trifluoromethyl)benzene; p-bis(trifluoromethyl)benzene; 2,4-dichlorobenzotrifluoride; fluorobenzene; 1,2-difluorobenzene; 1,3-difluorobenzene; 1,4-difluorobenzene; 1,2,4-trifluorobenzene; pentafluorobenzene; hexafluorobenzene; 2-fluorotoluene; 3-fluorotoluene; 4-fluorotoluene; 1,2-dichlorohexafluorocyclobutane; perfluorodimethylcyclobutane; 1,2-dichlorohexafluorocyclopenta-1-ene; 1,1,2,2,3,3,4-heptafluorocyclopentane; octafluorocyclopentane; pefluoromethylcyclohexane; perfluoro-1,2-dimethylcyclohexane; perfluoro-1,3-dimethylcyclohexane; periluoroethyl dimethyl cyclohexane; perfluoroalkane compound represented by the following formula: $CF_3(CF_2)_xCF_3$ (where x is an integer of 4 to 20); and periluoroalkylamine compound represented by the following formula: $N\{(CF_2)_yCF_3\}_3$ (where y is an integer of 1 to 20).

4. The process according to claim 1, wherein the reaction proceeds at a temperature of −25° C. to 50° C.

5. The process according to claim 1, wherein the amount of the fluorine-containing compound used as the reaction solvent is 0.05 to 20 g per 1 g of the aminoethyl α-substituted acrylate or aminoethyl α-substituted acrylate salt.

6. The process according to claim 1, wherein the base is at least one selected from the group consisting of trimethylamine, triethylamine, N,N-diethylmethylamine, tripropylamine, tributylamine, pyridine, 2,6-dimethylpyridine, N,N-dimethylaminopyridine, sodium carbonate, potassium carbonate, sodium hydroxide, and potassium hydroxide.

7. The process according to claim 1, wherein $R^1$ is a methyl group and $R^2$ is a trifluoromethyl group.

8. The process according to claim 1, wherein the fluorine-free compound is at least one selected from the group consisting of acetonitrile, benzonitrile, N,N-dimethylformamide, N,N-dimethylacetamide, N,N-dimethylimidazolydinone, dimethyl sulfoxide, diethyl ether, diisopropyl ether, dibutyl ether, tetrahydrofuran, triethylamine, and pyridine.

9. The process according to claim 8, wherein the fluorine-free compound is acetonitrile.

* * * * *